United States Patent [19]

Colella et al.

[11] 4,013,777

[45] Mar. 22, 1977

[54] BIS-PHENOXYPROPANOLAMINES

[75] Inventors: Donald F. Colella, Cornwells Heights, Pa.; Carl Kaiser, Haddon Heights, N.J.

[73] Assignee: SmithKline Corporation, Philadelphia, Pa.

[22] Filed: Aug. 22, 1975

[21] Appl. No.: 606,916

[52] U.S. Cl. .......................... 424/316; 260/501.18; 260/570.7; 260/340.2; 260/348 R; 424/330
[51] Int. Cl.² ..................... A01N 9/20; C07C 91/16
[58] Field of Search ....... 260/501.17, 340.2, 570.7, 260/501.18; 424/330, 316

[56] References Cited

UNITED STATES PATENTS

| | | | |
|---|---|---|---|
| 3,329,709 | 7/1967 | Schmid et al. | 260/501.18 |
| 3,673,187 | 6/1972 | Schromm et al. | 260/501.18 |
| 3,888,829 | 6/1975 | Bastian et al. | 260/501.18 |
| 3,888,898 | 6/1975 | Koppe et al. | 260/501.18 |

Primary Examiner—James O. Thomas, Jr.
Assistant Examiner—G. T. Breitenstein
Attorney, Agent, or Firm—Joseph A. Marlino; Richard D. Foggio; William H. Edgerton

[57] ABSTRACT

Bis-phenoxypropanolamine derivatives are prepared. These compounds have $\beta$-adrenergic stimulant activity particularly as selective bronchodilators.

5 Claims, No Drawings

BIS-PHENOXYPROPANOLAMINES

This invention relates to novel phenoxypropanolamine derivatives which have useful pharmacodynamic activity. More specifically, the compounds of this invention have utility as β-adrenergic stimulants with relatively greater activity on respiratory smooth muscle than on cardiac muscle. Therefore these compounds have direct bronchodilator action with minimal cardiac stimulation as demonstrated in standard pharmacological test procedures.

Two in vitro test systems used for determining selective β-stimulant activity are: (1) effect on spontaneous tone of guinea pig tracheal chain preparations as a measure of β-stimulant (direct relaxant) effect on airway smooth muscle, and (2) effect on rate of spontaneously beating right atria of the guinea pig as a measure of β-stimulant effect on cardiac muscle. The compounds of this invention have selective broncholdilating properties since they are active in (1) above at a dose lower than is required in (2) above resulting in a positive separation ratio.

The compounds of this invention are represented by the following general structural formula:

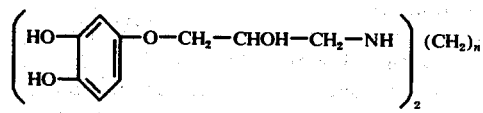

in which n represents from 2 to 8.

The compounds of this invention may be used in the form of a pharmaceutically acceptable acid addition salt having the utility of the free base. Such salts, prepared by methods well known to the art, are formed with both inorganic or organic acids, for example: maleic, fumaric, benzoic, ascorbic, pamoic, succinic, bis-methylenesalicylic, methanesulfonic, ethanedisulfonic, acetic, oxalic, propionic, tartaric, salicylic, citric, glyconic, aspartic, stearic, palmitic, itaconic, glycolic, p-aminobenzoic, glutamic, benzensulfonic, hydrochloric, hydrobromic, sulfuric, cyclohexylsulfamic, phosphoric and nitric acids.

Further the compounds of this invention contain two asymmetric carbon atoms and therefore exist as two diastereoisomers. One of the diastereoisomers may be resolved into d- and l-optical isomers. The other exists in a meso form. Unless otherwise specified in the description and accompanying claims, it is intended to include all isomers whether separated or mixtures thereof.

Separation of the diastereoisomers may be accomplished by conventional methods, such as chromatography or recrystallization of the mixture, either as the base or an acid addition salt from an appropriate solvent. Resolution of the optical isomers may be conveniently accomplished by fractional crystallization of their salts with optically active acids such as, for example, tartaric, camphor-10-sulfonic, 0,0-dibenzoyltartaric, 0,0-di(p-toluoyl)tartaric, camphoric, 2-pyrrolidone-5-carboxylic acids or N-acetyltryptophane from appropriate solvents.

The compounds of this invention are prepared as shown in the following sequence of reactions:

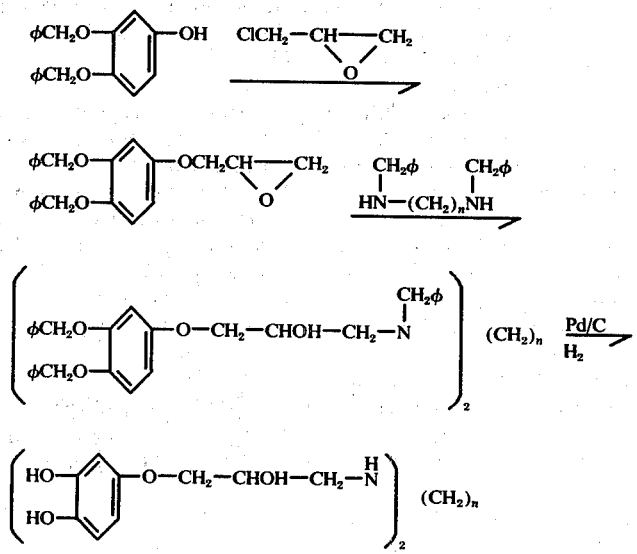

An advantageous compound of this invention is N,N'-bis[3,4-dihydroxyphenoxy)-2-hydroxypropyl]-1,6-diaminohexane which relaxes the spontaneous tone of guinea pig tracheal ring preparation at an $ED_{50}$ of 0.00414 mcg./ml. while increasing the rate of contraction of guinea pig right atria at an $ED_{25}$ of 0.029 mcg./ml. These activites give an absolute separation ratio of 7 which is a 14 fold improvement when compared to the corresponding activity of d,l isoproterenol (absolute separation ratio = 0.5) in similar in vitro preparations.

in which n is from 2 to 8. Thus as shown above, the appropriately substituted phenol is condensed with epichlorohydrin to yield an epoxide which upon treatment with the desired dibenzyldiamino alkane followed by catalytic hydrogenation, preferably with palladium-on-carbon gives the desired bis-phenoxypropanolamine.

Alternatively the bis-phenoxypropanolamine compounds can be prepared by substituting a primary diaminoalkane for the secondary dibenzyldiamino alkane.

The starting materials used herein are either known or are prepared by methods well known in the art from readily available materials.

The compounds of this invention may be administered orally or parenterally in conventional dosage unit forms such as tablets, capsules, injectables or the like, by incorporating the appropriate dose of a compound of Formula 1 with carriers according to accepted pharmaceutical practices. Preferably a compound or an acid addition salt thereof is administered orally to an animal organism in a tablet or capsule comprising an amount sufficient to produce β-adrenergic stimulant activity.

Each dosage unit will contain the active ingredient in an amount of from about 1 mg. to about 40 mg., preferably from about 3 mg. to about 20 mg. Advantageously equal doses will be administered 2 to 4 times daily with the daily dosage regimen being from about 2 mg. to about 160 mg.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. similarly the carrier or diluent can include any time delay material well known to the art, such as glyceryl monosterate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampul or an aqueous or nonaqueous liquid suspension.

Of particular applicability is an aerosol dispensing system wherein the active medicament is incorporated with Freon (fluorohydrocarbon) or other inert propellant in an aerosol container. Such an aerosol system will deliver a metered dose, administered once or twice at a time as needed. Such an aerosol system will deliver a metered dose of about 100 mcg. to about 650 mcg.

The foregoing is a general description of how to prepare the compounds of this invention. The following examples illustrate the preparation of specific compounds having β-adrenergic stimulant activity. However, this should not be construed as a limitation of the invention since appropriate variations in the starting materials will produce other products set forth hereinabove.

EXAMPLE 1

To a stirred solution of 6.1 g. of 3,4-dibenzyloxyphenol in 10 ml. of water and 1.53 g. of potassium hydroxide pellets is added 5.6 g. of epichlorohydrin in 60 ml. of ethanol. The solution is stirred at room temperature for 24 hours and then concentrated in vacuo. The residue is suspended in water and the mixture extracted with ether. The ether extracts are dried to yield 3-(3,4-dibenzyloxyphenoxy)-1,2-epoxypropane.

A solution of 5.5 g. of the above epoxypropane and 2.07 g. of N,N'-dibenzylhexamethylenediamine in 6.0 ml. of methanol is stirred at room temperature for 2 hours and then gently refluxed for 72 hours. The mixture is concentrated in vacuo. A solution of the residual liquid in ether is added to a solution of 1.7 g. of fumaric acid in 100 ml. of hot methanol to give N,N'-dibenzyl-N,N'-bis[3,4-dibenzyloxyphenoxy)-2-hydroxypropyl]-1,6-diaminohexane difumarate, m.p. 155°–161° C.

The above diaminohexane difumarate salt is suspended in water and the mixture is made alkaline with sodium hydroxide and extracted with ether. The ether solution is dried, decolorized and concentrated to leave the oily free base. A solution of 2.0 g. of the free base in 100 ml. of ethanol is mixed with 1.0 g. of palladium-on-carbon and the mixture is hydrogenated on a Parr apparatus at 25° C. and an initial hydrogen pressure of 60 psi. The reaction mixture is filtered and the filtrate is treated with a solution of 0.5 g. of fumaric acid in ethanol to yield bis-[3-(3,4-dihydroxyphenoxy)-2-hydroxypropyl]-1,6-diaminohexane fumarate as white crystals, m.p. 216°–218° C.

EXAMPLE 2

A solution of 5.1 g. of 3-(3,4-dibenzyloxyphenoxy)-1,2-epoxypropane and 0.6 g. of 1,4-diaminobutane in 60 ml. of methanol is stirred and refluxed for 72 hours. The resulting mixture is concentrated to leave an oily residue of N,N'-bis[3-(3,4-dibenzyloxyphenoxy)-2-hydroxypropyl]-1,4--diaminobutane.

A suspension of 7.5 g. of the latter diaminobutane in 100 ml. of methanol and 2.0 g. of 10% palladium-on-carbon is hydrogenated on a Parr apparatus at 25° C. and 60 psi until hydrogen uptake is completed. The mixture is filtered and the filtrate is concentrated in vacuo. Recrystallization of the residual solid from methanol yields N,N'-bis[3-(3,4-dihydroxyphenoxy)-2-hydroxypropyl]-1,4-diaminobutane.

EXAMPLE 3

Similarly substituting 1,2-diaminoethane, 1,3-diaminopropane, 1,5-diaminopentane, 1,6-diaminohexane, 1,7-diaminoheptane, or 1,8-diaminooctane as a starting material and proceeding with the ensuing reactions as described above in Example 2 yields the corresponding N,N'-bis[3-(3,4-dihydroxyphenoxy)-2-hydroxypropyl]-1,2-diaminoethane, N,N'-bis[3-(3,4-dihydroxyphenoxy)-2-hydroxypropyl]-1,3-diaminopropane, N,N'-bis[3-(3,4-dihydroxyphenoxy)-2-hydroxypropyl]-1,5-diaminopentane, N,N'-bis[3-(3,4-dihydroxyphenoxy)-2hydroxypropyl]1,6-diaminohexane, N,N'-bis[3-(3,4-dihydroxyphenoxy)-2-hydroxypropyl]-1,7-diaminoheptane, and N,N'-bis[3-(3,4-dihydroxyphenoxy)-2-hydroxypropyl]-1,8-diaminooctane.

EXAMPLE 4

| Ingredients | Mg. Capsule |
| --- | --- |
| N,N'-bis[3-(3,4-dihydroxyphenoxy)-2-hydroxypropyl]-1,6-diaminohexane fumarate | 5.0 mg. |
| Starch, U.S.P. | 50.0 mg. |
| Lactose, U.S.P. | 145.0 mg. |
| Magnesium Stearate, U.S.P. | 3.0 mg. |

The ingredients are thoroughly mixed and placed in a hard gelatin capsule. One capsule is taken three times a day.

What is claimed is:

1. A chemical compound of the formula:

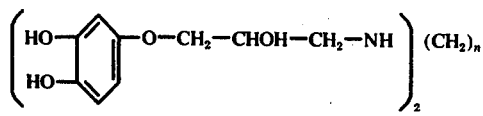

or a pharmaceutically acceptable acid addition salt of said compound, wherein n is from 2 to 8.

2. A chemical compound according to claim 1 in which n is 6 being the compound N,N'-bis[3-(3,4-dihydroxyphenoxy)-2-hydroxypropyl]-1,6-diaminohexane.

3. A chemical compound according to claim 2 in the form of a fumarate salt.

4. A pharmaceutical composition in dosage unit form having β-adrenergic stimulant activity comprising a pharmaceutical carrier and an effective amount of the chemical compound as defined in claim 1.

5. The method of producing β-adrenergic stimulant activity which comprises administering internally to animals requiring bronchodilation an amount sufficient to produce said activity a chemical compound as defined in claim 1.

* * * * *